(12) United States Patent
Liu et al.

(10) Patent No.: US 9,868,970 B2
(45) Date of Patent: Jan. 16, 2018

(54) **METHOD FOR IMPROVING GLCNAC PRODUCTION OF RECOMBINANT *BACILLUS SUBTILIS***

(71) Applicant: Jiangnan University, Wuxi, Jiangsu (CN)

(72) Inventors: Long Liu, Wuxi (CN); Jian Chen, Wuxi (CN); Guocheng Du, Wuxi (CN); Jianghua Li, Wuxi (CN); Yang Gu, Wuxi (CN); Yang Song, Wuxi (CN); Jieying Deng, Wuxi (CN); Yawen Zhao, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 94 days.

(21) Appl. No.: 15/205,014

(22) Filed: Jul. 8, 2016

(65) Prior Publication Data

US 2017/0130253 A1    May 11, 2017

(30) Foreign Application Priority Data

Nov. 10, 2015 (CN) .......................... 2015 1 0761678
Nov. 10, 2015 (CN) .......................... 2015 1 0762271
Jul. 1, 2016 (CN) .......................... 2016 1 0517961

(51) Int. Cl.
*C12N 9/88* (2006.01)
*C12P 19/26* (2006.01)
*C12N 9/12* (2006.01)
*C12N 9/00* (2006.01)

(52) U.S. Cl.
CPC ............ *C12P 19/26* (2013.01); *C12N 9/1205* (2013.01); *C12N 9/88* (2013.01); *C12N 9/93* (2013.01); *C12Y 207/0104* (2013.01); *C12Y 401/01032* (2013.01); *C12Y 604/01001* (2013.01)

(58) Field of Classification Search
CPC .................................. C12N 19/26; C12N 9/88
USPC .......................................................... 435/232
See application file for complete search history.

(56) References Cited

U.S. PATENT DOCUMENTS 9,605,283 B2 * 3/2017 Walther .................... C12P 7/18

* cited by examiner

*Primary Examiner* — Tekchand Saidha
(74) *Attorney, Agent, or Firm* — SZDC Law P.C.

(57) ABSTRACT

The invention provides an effective method for improving N-acetylglucosamine (GlcNAc) production by engineered *B. subtilis* Deletion of phosphoenolpyruvate carboxykinase encoding gene pckA and encoding pyruvate kinase gene pyK in recombinant GlcNAc-producing strain BSGNK-PxylA-glmS-P43-GNA1 (BSGNK) is first performed to enhance GlcNAc production, followed by overexpression of pyruvate carboxylase encoding gene pycA for facilitating cell growth. Finally, the GlcNAc production of the recombinant strain BPTS3 reached to 11.3 g/L, which was 1.84-fold of BSGNK. This method can be used for improve cellular property of engineered *B. subtilis* for GlcNAc production, which can be further applied to industrial production of GlcNAc.

12 Claims, 2 Drawing Sheets

SEQUENCE LISTING

<160> NUMBER OF SEQ ID NOS: 3

<210> SEQ ID NO 1
<211> LENGTH: 2656
<212> TYPE: DNA
<213> ORGANISM: Artificial Sequence
<220> FEATURE:
<223> OTHER INFORMATION: DNA sequence of the pckA disrupt cassette

<400> SEQUENCE: 1

| | | | | | |
|---|---|---|---|---|---|
| acggacttca | cttaggcggc | gggctaattt | atgggcaagt | gaaattggaa gaggcataag | 60 |
| ctctttcgtt | tcgttgcacg | cataaccgaa | cattaatcct | tggtcacccg caccaatcgc | 120 |
| ttcaatttct | tcgtcgctca | ttgtgccttc | acgggcttca | agcgcttggt ctacgcccat | 180 |
| cgcgatatca | gcagactgct | catcaattga | tgttaaaacc | gcacaagttt ccgcatcaaa | 240 |
| tccgtatttt | gcacgtgtgt | atccgatttc | tttaatggtt | tggcgaaccg ttttcggaat | 300 |
| gtcaacatac | gtagaagttg | tgatctctcc | gcttacaaga | accaaacctg ttgtcacaga | 360 |
| tgtttcacaa | gcaacacgcg | cgttagggtc | tttctttaaa | atttcatcta aaatgctgtc | 420 |
| agaaatctgg | tcacagattt | tatccggatg | cccctccgta | acagattctg atgtaaataa | 480 |
| acgacgattt | ttactcatga | tttgcttcct | cctgcacaag | gcctcccgaa agaccttgta | 540 |
| tatatgatac | ggaactcgct | ccctcttata | caatgtacag | ttatattaga gaatgttaat | 600 |
| tggcatattt | atgaaataaa | aaacctttt | ccatcgagga | aagggtttgg tctttgtgcc | 660 |
| tttcactctt | atcgctcaag | gaatcataca | accttgcaac | aggttagcac cttggttgtc | 720 |
| tcactcagtt | gaacataata | aataacagag | aaaccggttg | ctgggcttca tagggcctgt | 780 |
| ccctccgcca | gctcgggata | agagtatccg | ctcaatgaaa | tatcttatcg taaagggtt | 840 |
| tgcaatgtca | atatgattca | gaagaaatag | gcacctatat | tgagggaaaa caatggaaat | 900 |
| gcacacacaa | aaaacaataa | atagtataga | ctatttgaaa | atatatgtta tactaattca | 960 |
| caattagcaa | aacacaaaaa | acgataaagg | aaggtttcat | gagcggataa caatttcaca | 1020 |
| caggaaacag | ctatgaccat | gattacgaat | tcgagctcgg | tacccgggga tcctctagag | 1080 |
| attctaccgt | tcgtatagca | tacattatac | gaagttatct | tgatatggct ttttatatgt | 1140 |
| gttactctac | atacagaaag | gaggaactaa | atatggccaa | gttgaccagt gccgttccgg | 1200 |
| tgctcaccgc | gcgcgacgtc | gccggagcgg | tcgagttctg | gaccgaccgg ctcgggttct | 1260 |
| cccgggactt | cgtggaggac | gacttcgccg | gtgtggtccg | ggacgacgtg accctgttca | 1320 |
| tcagcgcggt | ccaggaccag | gtggtgccgg | acaacaccct | ggcctgggtg tgggtgcgcg | 1380 |
| gcctggacga | gctgtacgcc | gagtggtcgg | aggtcgtgtc | cacgaacttc cgggacgcct | 1440 |
| ccgggccggc | catgaccgag | atcggcgagc | agccgtgggg | gcgggagttc gccctgcgcg | 1500 |
| acccggccgg | caactgcgtg | cacttcgtgg | ccgaggagca | ggactgaata acttcgtata | 1560 |
| gcatacatta | tacgaacggt | agaatcgtcg | acctgcaggc | atgcaagctt ggcactggcc | 1620 |
| gtcgttttac | aacgtcgtga | ctgggaaaac | cctggcaaaa | caaaagccaa gagcaattat | 1680 |
| gctcttggct | tgttttaatt | gacggaatgc | aaagaagtca | gcttgtatgt aatgatggtc | 1740 |
| cggccttctt | cccattgaag | cttctgcact | tcagctgtgc | ctgactttc gccaaacttt | 1800 |
| gttttgcgta | catccattgg | aatctccatc | ggatatactc | ggtatccgtc cttctctaac | 1860 |
| gtgaatatat | ttcatctat | gcgaacttct | tttccttttg | tcacaatcag tgtattaaat | 1920 |
| tcaacaggca | ttcccaaagt | gaaatcccct | ttcgttctct | ttttcttta tcataacata | 1980 |
| tttcactgtc | agcggttttt | catccattgt | gtgagctgcc | gcacgatacg ccggtttct | 2040 |

| | |
|---|---:|
| tttggcggga aataatgtgt gaatgtactg tagtaccatg tttccaccgg cttatgcagt | 2100 |
| tgttttagct tctcttctaa taaataggaa tgctgaatcg aaacattttg gtcttttct | 2160 |
| ccatggatta acagcacggg agcctgaatt ttgtttactt ggtcaaacgg tgtcctccat | 2220 |
| tgatattcct caggcacctt tttcggtgtt ccgccgatga ctcttttcat cattcgccgc | 2280 |
| aaatcctgcc gctcctcgta tgtaagaatc atatcactga cgcctcccca ggaaacaaat | 2340 |
| gaagctgcct gcccgcccat ttcgatcgca gtgagcattc ccataattcc gccgcgggaa | 2400 |
| aaaccgaaga tatggattct atccttcttg acatttgggt gctgctgaag caggcgaaaa | 2460 |
| gcagaaaatg catcctccct gtcttctccg gcaaaatcct cattgccttc tcctccttga | 2520 |
| ttgcctctgt aaaaggagc aaacaccaca aacccttggg atgcaaactg ataatccgg | 2580 |
| cccggccgaa ccatgcccac gcttttaatc ccgccgcgca aatataaaaa tccgtcatat | 2640 |
| tgtcccggtt ccgccg | 2656 |

<210> SEQ ID NO 2
<211> LENGTH: 2656
<212> TYPE: DNA
<213> ORGANISM: Artificial Sequence
<220> FEATURE:
<223> OTHER INFORMATION: DNA sequence of the pyk disrupt cassette

<400> SEQUENCE: 2

| | |
|---|---:|
| gaaacgaata ggggtattaa cgagcggcgg ggattccccg ggaatgaacg cagcagttcg | 60 |
| cgcagtagtc agaaaagcga tctatcatga cgttgaagtt tacggtattt acaacggata | 120 |
| cgcgggattg atcagcggaa agattgaaaa gcttgaactc ggatcagtag gcgatattat | 180 |
| acatcgtgga gggactaagc tttatacggc gagatgtcct gaattcaaaa cagttgaagg | 240 |
| ccgtgaaaaa gggatagcaa acttgaagaa gcttggtatt gaaggccttg ttgttatcgg | 300 |
| tggagacggt tcctatatgg gtgcgaaaaa attaacggaa cacgggtttc catgtgtagg | 360 |
| tgtaccgggt acaattgata tgacattcc gggcactgat tttacaatcg gtttcgatac | 420 |
| agctttaaat acagtaattg acgcaattga taagattcgc gatacagcga cttctcatga | 480 |
| acgtacatat gtaatcgaag taatgggccg tcatgccggc gatatcgcat tgtgggccgg | 540 |
| tcttgcaggg ggcgcagaat cgatcttaat ccctgaggca gactatgaca tgcacgaaat | 600 |
| cattgcccgc ttaaaacgcg gccacgaacg cggcaagaag cacagtatta ttattgttgc | 660 |
| cgaaggtgta ggcagcggtg ttgaattcgg gaaacgcatt gaagaagaaa caaatcttga | 720 |
| aactagggta tctgtattgg gccatatcca gcgcggaggt tctccgagtg ctgctgaccg | 780 |
| tgtgttggca agccgtctcg gcgcatatgc agttgaactg ctgcttgaag gaaaaggcgg | 840 |
| acgctgtgta ggtatacaaa acaataagct tgtagaccat gatattatag aaatacttga | 900 |
| gacaaaacac acagttgagc aaaacatgta tcagctttca aaagaactgt ctatctaatg | 960 |
| tacagctgaa ggctgaagat ttcagaagga agtgaaccaa gagcggataa caatttcaca | 1020 |
| caggaaacag ctatgaccat gattacgaat tcgagctcgg tacccgggga tcctctagag | 1080 |
| attctaccgt tcgtatagca tacattatac gaagttatct tgatatggct ttttatatgt | 1140 |
| gttactctac atacagaaag gaggaactaa atatggccaa gttgaccagt gccgttccgg | 1200 |
| tgctcaccgc gcgcgacgtc gccggagcgg tcgagttctg gaccgaccgg ctcgggttct | 1260 |
| cccgggactt cgtggaggac gacttcgccg gtgtggtccg gacgacgtg acccgtgttca | 1320 |
| tcagcgcggt ccaggaccag gtggtgccgg acaacaccct ggcctgggtg tgggtgcgcg | 1380 |

-continued

```
gcctggacga gctgtacgcc gagtggtcgg aggtcgtgtc cacgaacttc cgggacgcct      1440
ccgggccggc catgaccgag atcgcgagc agccgtgggg gcgggagttc gccctgcgcg       1500
acccggccgg caactgcgtg cacttcgtgg ccgaggagca ggactgaata acttcgtata      1560
gcatacatta tacgaacggt agaatcgtcg acctgcaggc atgcaagctt ggcactggcc      1620
gtcgttttac aacgtcgtga ctgggaaaac cctggcttac aggtgaaaat ggaaggggaa      1680
tcccttcctt ttctctttat catgcctttt gttgaacaga acgtgttaca cgtgtggggg      1740
gcttggatat gagattttg ttttgctttt ttattgtgtt ccggcaata gaaatcggta        1800
tattcctatt tttaggaaat ctgattggta ttttgccgac agttctattc atgattctga     1860
ctggcattat cggcgcagca gctgcaaaaa aacaaggaac cgaagtgtat tataaggttc      1920
agcgtgatct tcaatatggc aaaatgccgg gagaagcgat tgctgacggt ctgtgcattt      1980
tcattggcgg tctattgctg atgcttccgg gcttttatc agatttggcc ggcgcctgtc      2040
ttcttatccc gtttacccgc ggctggtgta agccgattct gttcaaatgg ctgagaggaa      2100
tgtcgaagaa taagcggatc atcatcaaat aaaaaacggc agccatgaaa aaacggctgc     2160
cgttttattt ttgctgaacg gtgatatagg accatatttc ttttaatgcg cctgttgtga     2220
tgaaagcttg gatgatgacg agtacagccg gtcccgcaat cagtcctaaa acccgaata     2280
atttaaagcc ggcaaacagg gcgatgagtg ttgccagcgg atcgatcccg atagatttac     2340
ttagtatctt gggctctgtc agctgccgct gaataagaac gacgaggtac aggataccaa    2400
ttccgattgc ttggggcagc tggcccgtaa tcgataaata caaaatccag ggcacaaata    2460
cggagccggc acctaagtaa gggagaagat ctacaagccc gattaaaaaa gcaattgttg     2520
cggcgtgttc aacctttaag agagaaaggc cgataaatac aatcaccatc gtgatgaaaa     2580
cgaggacggc ttgtgctttg ataaaaccag tcattgcttt ttttaattcg ctgctgattg     2640
ctttgctgtt agctgt                                                      2656
```

<210> SEQ ID NO 3
<211> LENGTH: 3447
<212> TYPE: DNA
<213> ORGANISM: Artificial Sequence
<220> FEATURE:
<223> OTHER INFORMATION: DNA sequence of the pycA disrupt cassette

<400> SEQUENCE: 3

```
ttgtctcagc aatcgataca aaaagtatta gtagcaaaca ggggagaaat tgcaatccga       60
atattccggg cgtgtaccga gttgaatatt cgtacagttg cggtctattc aaaagaagat     120
tccggttcct accatcggta caaagcggat gaagcatact tggtcggtga agggaaaaaa    180
ccgattgatg cttacctgga tattgaaggt atcattgata ttgcgaaaag aaacaaagtc     240
gatgcaattc atccgggata cggtttctta tctgaaaata ttcatttgc gagacgatgt      300
gaagaagaag gcatcgtatt catagggcca aaatccgagc atctcgatat gtttggtgac    360
aaggtaaaag cgcgtgagca ggcagaaaaa gcgggaatcc ccgtgattcc gggaagcgac    420
ggtcctgccg aaacgcttga agccgtcgaa caatttggac aagctaacgg ttatccgatc    480
atcattaaag cctcgcttgg cggcggcggc cgcggtatgc ggattgtcag atctgaaagt    540
gaagttaaag aagcatatga gcgtgctaaa tcagaggcga agcagccctt ggcaatgat    600
gaagtttatg tagaaaaatt aattgagaat ccgaaacata ttgaggttca ggtcattgga     660
gacaagcagg gcaatgtcgt ccatcttttt gagagggatt gctccgttca aagacgccat    720
caaaaagtca ttgaagtggc gccgagtgtc tcgctgtcac ctgaattaag ggaccaaatt    780
```

```
tgtgaggctg cagttgcgct tgccaaaaat gtaaactata taaatgcggg gacggtcgaa    840
ttccttgttg caaacaacga gttctacttt attgaagtaa atcctcgcgt acaagttgaa    900
cacacgataa cagaaatgat tactggtgtc gatattgttc aaactcagat ccttgttgcc    960
caagggcaca gccttcacag caaaaaagta aatattcctg agcaaaagga cattttttaca   1020 atcggctatg ccattcagtc acgggttacg actgaggatc cgcaaaatga tttcatgcct   1080
gatacaggaa aaatcatggc ttaccgctca ggcggcggtt ttggtgtccg tcttgatacc   1140
ggaaacagct tccagggcgc cgtgatcaca ccatactatg attcacttct cgttaagctt   1200
tcaacttggg ctttaacgtt tgaacaggca gctgccaaaa tggtgcgaaa ccttcaggag   1260
tttagaatca gaggcataaa aacgaacatt ccgttccttg agaacgttgc aaagcatgag   1320
aagttcctga cagggcaata tgatacatct ttcattgata caacgcctga attatttaat   1380
ttccctaaac aaaaagaccg cggaacgaaa atgctcactt acatcggcaa tgtgacagtg   1440
aacggcttcc ctggaatcgg gaaaaaagaa aaaccggcgt tgacaaaacc gttaggcgta   1500
aaggtagacg ttgatcagca gcctgccaga ggaacaaagc aaattctcga tgaaaaaggt   1560
gcagaagggc ttgcaaattg ggttaaggag cagaaatctg tccttttaac tgatacgaca   1620
ttcagggatg cccaccaatc gttattggca actagaatca gatcgcatga tttgaaaaaa   1680
atcgcaaatc cgacggctgc gttatggcct gaactattca gtatgaaat gtggggaggc   1740 gcgaccttcg atgtagccta ccgattcctg aaagaagatc cgtggaaacg tttggaagat   1800
cttcgcaaag aagtgccgaa taccttattc cagatgttgc ttcgctcatc aaatgcggtc   1860
ggctatacga attatccgga caatgtgatt aaagaatttg tgaagcaatc agctcaatcc   1920
ggtattgatg tgtttcgtat tttcgacagc ttaaactggg taaaagggat gacgttagcc   1980
attgatgctg ttagggatac cggcaaagtg gcagaagctg cgatttgtta tacgggagat   2040
atccttgaca gaaccggac gaagtacgac cttgcatatt atacatcgat ggcgaaggag   2100
cttgaggcgg ccggagccca tattctcggg attaaagata tggcagggct gttaaaaccg   2160
caggctgcat atgagctcgt ttctgcgttg aaagaaacga tcgacattcc ggttcacctt   2220
catacgcatg atacgagcgg aaacggtatt tatatgtatg cgaaagctgt tgaagccggc   2280
gttgatatca tagacgtggc ggtcagctca atggcgggat taacgtcaca gcctagcgcg   2340
agcggatttt atcatgcgat ggaaggcaac gaccgccgtc cggaaatgaa tgtccaaggc   2400
gttgaattgc tgtcccaata ttgggagtcg gtgcgtaaat attatagtga atttgaaagc   2460
ggaatgaagt ctccgcatac tgaaatttat gaacacgaaa tgccagggg ccaatacagc   2520 aacctgcagc agcaagccaa gggagtaggc cttggcgacc gctggaacga agtcaaggaa   2580
atgtacagac gcgtgaacga tatgttcggt gacatcgtca aggtaacgcc ttcctcaaaa   2640
gtagtcggag atatggcact ctacatggtg caaaacaatc tgactgaaaa agacgtttac   2700
gaaaaaggtg aatctttaga tttccctgat tctgtcgtgg agcttttaa aggaaatatc   2760 ggccagcctc atggcggatt cccagaaaaa ctgcaaaagc tgatcttaaa agggcaggag   2820
ccgattacag tcagaccggg cgaactgctt gagccggtgt catttgaagc gatcaaacag   2880
gaatttaaag agcagcataa cttggaaatt tcagatcagg atgctgtggc atatgccctt   2940
tatcctaaag tcttcactga ttatgtgaaa acgacagaaa gctatggaga catctcggta   3000
ttagatacac cgacattctt ctacggtatg acattaggtg aagagataga agttgaaatt   3060
gagcgcggca aaacgctgat cgttaagctg atttcaatcg gtgagcctca gcctgatgcc   3120
```

```
acccgcgtcg tttatttcga actcaacggg cagccgcgtg aagtagtcat taaagatgaa    3180
agcattaagt cttccgttca ggaaaggctg aaagcagacc ggacaaatcc aagccacatc    3240
gcagcttcca tgcctggaac agttattaag gtattggctg aagcaggcac aaaagtcaat    3300
aaaggtgatc atttgatgat taatgaagcg atgaaaatgg aaacaacggt tcaggcgcct    3360
ttctcaggaa caatcaagca ggttcatgtg aaaaatggtg agccgatcca aacgggagat    3420
ctgctccttg aaattgaaaa agcataa                                        3447
```

METHOD FOR IMPROVING GLCNAC PRODUCTION OF RECOMBINANT *BACILLUS SUBTILIS*

CROSS-REFERENCE TO RELATED APPLICATIONS

The present application claims the benefit of Chinese Patent Application Nos. 201510761678.6, filed on Nov. 10, 2015, 201510762271.5, filed on Nov. 10, 2015, and 201610517961.9, filed on Jul. 1, 2016, all of which are incorporated by reference for all purposes as if fully set forth herein.

REFERENCE TO A SEQUENCE LISTING

The present application contains a Sequence Listing which has been submitted via EFS-Web and is hereby incorporated by reference in its entirety. The Sequence Listing is an ASCII file named 100150002.txt, and is 11,616 bytes in size.

FIELD OF THE INVENTION

The present invention relates to the field of genetic engineering, more particularly to a method for enhancing N-acetylglucosamine (GlcNAc) production in genetically modified *B. subtilis* by microbial fermentation.

DESCRIPTION OF THE RELATED ART

GlcNAc is a pharmaceutically and nutraceutically useful compound, which was widely used for treatment of osteoarthritis and maintaining health of the joints. Biological production of GlcNAc via microbial fermentation by engineered *B. subtilis* emerged as a promising method to produce GlcNAc in a safe and sustainable approach. The phosphoenol-pyruvate (PEP)-sugar phosphotransferase system (PTS) is the main glucose transportation system in *B. subtilis*. Despite efficient glucose uptake by the phosphotransferase system (PTS), 1 mol of pyruvate will be produced for each mole of internalized glucose. Rather, pyruvate also can be produced by central metabolism. As a consequence, much glucose would be used to synthesize pyruvate, which leads to low GlcNAc titer and low yield for the conversion of glucose to GlcNAc. Noticeably, low GlcNAc titer of engineered *B. subtilis* restricted the application for industrial production. To move a step forward for microbial GlcNAc fermentation in industrial conditions, GlcNAc titer and yield should be improved.

SUMMARY OF THE INVENTION

In order to solve the above problems of the prior art, one object of the present application is to provide a method for improving GlcNAc production of recombinant *Bacillus Subtilis*.

For the above technical purpose and effects, the application utilizes the following technical solutions:

A method for improving GlcNAc production of recombinant *Bacillus Subtilis*, the method comprises steps of deletion of phosphoenolpyruvate carboxykinase pckA, deletion of pyruvate kinase pyk, as well as overexpression of pyruvate carboxylase pycA.

Preferably, the above recombinant *Bacillus Subtilis* is BSGNK which is obtained by overexpressing a glucosamine-6-phosphate synthase glms under the control of an inducible promoter PxylA and GlcN-6-phosphate N-acetyltransferase GNA1 under the control of a constitutive promoter P43 in the basis of deleting nagP, gamP, nagA, nagB, gamA and glck of *Bacillus Subtilis* 168. In a specific embodiment, the BSGNK is constructed by the method disclosed in the China Patent Application Ser. No. 201510394205.7.

In an embodiment, deletion of phosphoenolpyruvate carboxykinase encoding gene pckA comprises step of constructing a pckA disrupt cassette, the pckA disrupt cassette includes a pckA upstream homology sequence, a zeocin resistant gene expression cassette, and a pckA downstream homology sequence, from *Bacillus Subtilis* 168. Wherein DNA sequence of phosphoenolpyruvate carboxykinase encoding gene pckA is as shown in NCBI-Gene ID: 937235.

In some embodiments, the length of the pckA upstream homology sequence is 0.5-1.5 kb, preferably 0.5-1.0 kb, and more preferably 1.0 kb.

In some other embodiments, the length of the pckA downstream homology sequence is 0.5-1.5 kb, preferably 0.5-1.0 kb, and more preferably 1.0 kb.

In a specific embodiment, the DNA sequence of the pckA disrupt cassette is as shown in SEQ ID NO.1.

In an embodiment, deletion of pyruvate kinase encoding gene pyk comprises step of constructing a pyk disrupt cassette, the pyk disrupt cassette includes a pyk upstream homology sequence, a zeocin resistant gene expression cassette, and a pyk downstream homology sequence, from *B. subtilis* 168. Wherein the DNA sequence of pyruvate kinase encoding gene pyk is as shown in NCBI-Gene ID: 936596.

In some embodiments, the length of the pyk upstream homology sequence is 0.5-1.5 kb, preferably 0.5-1.0 kb, and more preferably 1.0 kb.

In some other embodiments, the length of the pyk downstream homology sequence is 0.5-1.5 kb, preferably 0.5-1.0 kb, and more preferably 1.0 kb.

In a specific embodiment, the DNA sequence of the pyk disrupt cassette is as shown in SEQ ID NO.2.

In an embodiment, the pyruvate carboxylase pycA is overexpressed under the control of a constitutive promoter P43 and replacing a start codon GTG with ATG. The DNA sequence of pyruvate carboxylase encoding gene pycA is shown in NCBI-Gene ID: 935920.

In another embodiment, overexpression of pyruvate carboxylase encoding gene pycA comprises step of constructing a pycA overexpressed cassette which includes a pycA upstream homology sequence, a zeocin resistant gene expression cassette, a P43 strong promoter, and a pycA sequence with replacing the start codon GTG with ATG, from *B. subtilis* 168.

In some embodiments the length of the pycA upstream homology sequence is 0.5-5 kb, preferably 0.5-1.0 kb, and more preferably 1.0 kb.

In a specific embodiment, the DNA sequence of the pycA overexpressed cassette is shown as SEQ ID NO.3.

In a preferable embodiment of the invention, the method comprises the following steps:

(1) deleting phosphoenolpyruvate carboxykinase encoding gene pckA of recombinant *Bacillus Subtilis* BSGNK to block the anaplerosis from PEP to oxaloacetate, to obtain a recombinant strain BPTS1;

(2) deleting pyruvate kinase encoding gene pyk of the recombinant strain BPTS1 to block the synthesis from PEP to pyruvate by glycolysis pathway, to obtain a recombinant strain BPTS2; and (3) overexpressing pyruvate carboxylase encoding gene pycA of recombinant strain BPTS2 to facilitate cell growth, to obtain a recombinant strain BPTS3.

In a more preferable embodiment, the step (1) specifically comprises:

utilizing a primer pckA-F/pckA-R to amplify a pckA disrupt cassette which includes a pckA upstream homology sequence, a zeocin resistant gene expression cassette, and a pckA downstream homology sequence, from *Bacillus Subtilis* 168;

transforming the amplified pckA disrupt cassette into BSGNK, and selecting a positive transformant;

introducing a vector pTSC into the positive transformant to delete the resistance marker cassette; and evicting the plasmid pTSC to obtain the recombinant strain BPTS1.

In a more preferable embodiment, the step (2) specifically comprises:

utilizing a primer pyk-F/pyk-R to amplify a pyk disrupt cassette which includes a pyk upstream homology sequence, a zeocin resistant gene expression cassette, and a pyk downstream homology sequence, from *Bacillus Subtilis* 168;

transforming the amplified pyk disrupt cassette into the recombinant strain BPTS1, and selecting a positive transformant;

introducing a vector pTSC into the positive transformant to delete the resistance marker cassette; and evicting the plasmid pTSC to obtain the recombinant strain BPTS2.

In a still more preferable embodiment, the step (3) specifically comprises:

utilizing a primer pycA-F/pycA-R to amplify a pycA overexpressed cassette which includes a pycA upstream homology sequence, a zeocin resistant gene expression cassette, a P43 strong promoter, and a pycA sequence with replacing the start codon GTG with ATG, from *Bacillus Subtilis* 168;

transforming the amplified pycA overexpressed cassette into the recombinant strain BPTS2, and selecting a positive transformant;

introducing a vector pTSC into the positive transformant to delete the resistance marker cassette; and evicting the plasmid pTSC to obtain the recombinant strain BPTS3.

Due to the above technical solutions, the embodiments of the present invention have the following advantages as compared with the prior art: the method disclosed in the specification is more effective for improving production of N-acetylglucosamine (GlcNAc). Specially, the GlcNAc production of the recombinant strain BPTS3 reached to 11.3 g/L, which was 1.84-fold of that of the starting strain BSGNK. Furthermore, the method also greatly increases the yield for the conversion of glucose to GlcNAc and the GlcNAc Productivity. So, this method can be used for improving cellular property of engineered *B. subtilis* for GlcNAc production, which can be further applied to industrial production of GlcNAc.

DESCRIPTION OF THE PREFERRED EMBODIMENTS

Figure 1:
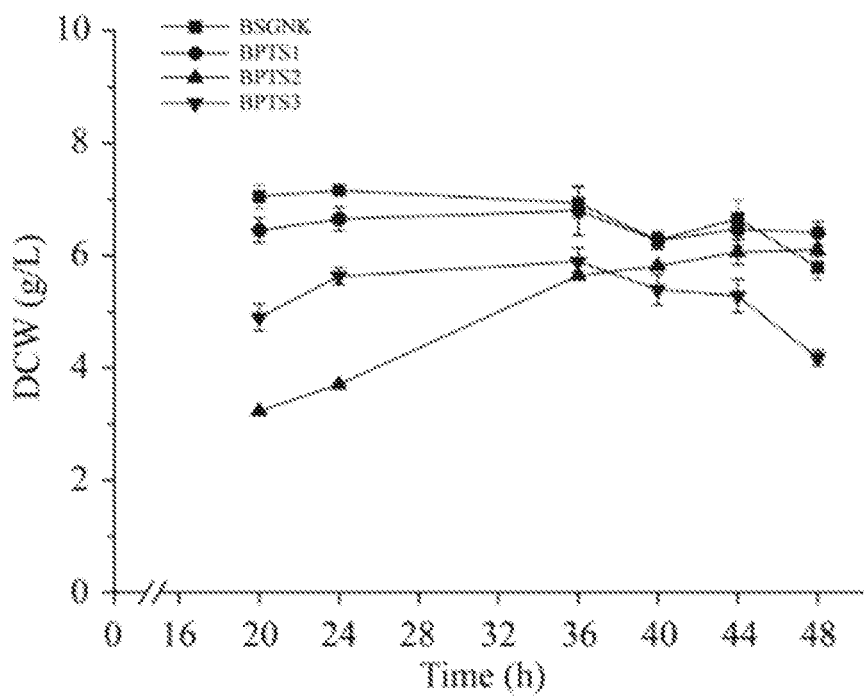
FIG. 1 is a graph showing the comparison of cell growth of the strains BSGNK, BPTS1, BPTS2 and BPTS3 during fermentation.

The invention will be further illustrated in more detail with reference to accompanying drawings. It is noted that, the following embodiments are intended for purposes of illustration only and are not intended to limit the scope of the invention.

The present invention provides a g method for improving GlcNAc production in engineered *B. subtilis*. Specifically, the method comprises the steps of deletion of phosphoenolpyruvate carboxykinase encoding gene pckA, deletion of pyruvate kinase encoding gene pyk and overexpression of pyruvate carboxylase encoding gene pycA in a recombinant *Bacillus Subtilis*. In a preferable embodiment, the starting strain is BSGNK-PxylA-glmS-P43-GNA1 (BSGNK), and the finally obtained strain with improved GlcNAc production and yield is BPTS3.

Embodiment 1

Deletion of Phosphoenolpyruvate Carboxykinase Encoding Gene pckA of the Strain BSGNK to Block the Anaplerosis from PEP to Oxaloacetate, to Obtain the Recombinant Strain BPTS1, Wherein BSGNK is Obtained by the Method Disclosed in China Patent Application Ser. No. 201510394205.7.

Deletion of phosphoenolpyruvate carboxykinase pckA was first performed to block the anaplerosis from PEP to oxaloacetate. Specifically, a primer pckA-F (ACGGACT-TCACTTAGGCGGC)/pckA-R (GACGGATTTTTAT-ATTTGCGCG) was used to amplify a pckA disrupt cassette, which included a pckA upstream homology sequence (1 kb), a zeocin resistant gene expression cassette, and a pckA downstream homology sequence (1 kb), from *B. subtilis* 168. DNA sequence of the pckA disrupt cassette is as shown in SEQ ID NO.1. The amplified pckA disrupt cassette was transformed into the strain BSGNK, and transformants were selected on LB plate with 30 μg/mL zeocin. Positive transformants with pckA gene deletion were further verified by colony PCR with primers pckA-F/pckA-R. The vector pTSC was introduced into the Positive transformants to promote the recombination between lox71 and lox66, thereby deleting the resistance marker cassette. Plasmid pTSC was then evicted by incubating at 50° C. for 12 h to obtain the strain without the selected marker and plasmid, naming BPTS1.

Embodiment 2

Deletion of Pyruvate Kinase Encoding Gene pyK in the Strain BPTS1 to Block the Synthesis from PEP to Pyruvate by Glycolysis Pathway.

Deletion of pyruvate kinase pyK was performed to block the synthesis from PEP to pyruvate by glycolysis pathway. Specifically, the primer pyK-F (ACGAATAGGGGTAT-TAACGAGCG)/pyK-R(CAGCTAACAG-CAAAGCAATCAGC) was used to amplify a pyK disrupt cassette, which included a pyK upstream homology sequence (1 kb), a zeocin resistant gene expression cassette, and a pyK downstream homology sequence (1 kb), from *B. subtilis* 168. DNA sequence of the pyK disrupt cassette is as shown in SEQ ID NO.2. The amplified pyK disrupt cassette was transformed into the strain BPTS1, and transformants were selected for on LB plate with 30 μg/mL zeocin. Positive transformants with pyK gene deletion were further verified by colony PCR with primers pyK-F/pyK-R. The vector pTSC was introduced into the Positive transformants to promote the recombination between lox71 and lox66, thereby deleting the resistance marker cassette. Plasmid pTSC was then evicted by incubating at 50° C. for 12 h to obtain the strain without the selected marker and plasmid, naming BPTS2.

Embodiment 3

Overexpression of Pyruvate Carboxylase Encoding Gene pycA of the Strain BPTS2 to Facilitate Cell Growth.

Overexpression of pyruvate carboxylase encoding gene pycA was performed to facilitate cell growth. Specifically, a primer pycA-F (GCAGAGCTGGTTTAAAATCGG)/pycA-R(CCCAAGTTGAAAGCTTAACGAGA) was used to amplify a pycA overexpressed cassette, which included a pycA upstream homology sequence (1 Kb), a zeocin resistant gene expression cassette, a P43 strong promoter, a pycA sequence with replacing the start codon GTG with ATG, from B. subtilis 168. DNA sequence of pycA overexpressed cassette is as shown in SEQ ID NO.3. The amplified pycA overexpressed cassette was transformed into the strain BPTS2, and transformants were selected on LB plate with 30 μg/mL zeocin. Positive transformants with pycA gene overexpression were further verified by colony PCR with primers pycA-F/pycA-R. The vector pTSC was introduced into the positive transformants to promote the recombination between lox71 and lox66, thereby deleting the resistance marker cassette. Plasmid pTSC was then evicted by incubating at 50° C. for 12 h to obtain the strain without the selected marker and plasmid, naming BPTS3.

Shake-Flask Fermentation of the Strains BSGNK, BPTS1, BPTS2 and BPTS3.

The seed medium was Luria-Bertani broth or agar plates containing (g/L): tryptone 10, yeast extract 5, and NaCl 10. The fermentation medium contained (g/L): tryptone 6, yeast extract 12, $(NH_4)SO_4$ 6, $K_2HPO_4 \cdot 3H_2O$ 12.5, $KH_2PO_4$ 2.5, $MgSO_4 \cdot 7H_2O$ 3, $CaCO_3$ 5, glucose 60, and 15 ml of trace metal solution. The trace metal solution contained (per liter of 5M HCl) (g/L): $FsSO_4 \cdot 7H_2O$ 4.0, $CaCl_2$ 4.0, $MnSO_4 \cdot 5H_2O$ 1.0, $CoCl_2 \cdot 6H_2O$ 0.4, $NaMnO_4 \cdot 2H_2O$ 0.2, $ZnSO_4 \cdot 7H_2O$ 0.2, $AlCl_3 \cdot 6H_2O$ 0.1, $CuCl_2 \cdot H_2O$ 0.1, and $H_3BO_4$ 0.05. Seed culture was carried out in 250-mL shake flasks each containing 20 ml of seed medium with shaking at 200 rpm and 37° C. for 12 h. The seed culture (5 ml) was inoculated into 500-mL shake flasks containing 95 mL of fermentation medium. And then, fermentation was carried out at 220 rpm and 37° C. for 48 h on rotary shakers. When the optical density at 600 nm (OD600) reached 0.4, xylose was added to the medium to a final concentration of 5 g/L to induce gene expression under the control of the xylose-inducible $P_{xyla}$ promoter.

Embodiment 4

Effects of Deletion of Phosphoenolpyruvate Carboxykinase Encoding Gene pckA on Cell Growth and GlcNAc Production To determine the effects of deletion of phosphoenolpyruvate carboxykinase encoding gene pckA on cell growth and GlcNAc production, the strain BPTS1 and BSGNK were inoculated with an inoculum size of 5% (v/v) into 500-mL shake flasks each containing 95 mL of fermentation medium. And then, fermentation was carried out at 220 rpm and 37° C. for 48 h on rotary shakers.

Figure 2:
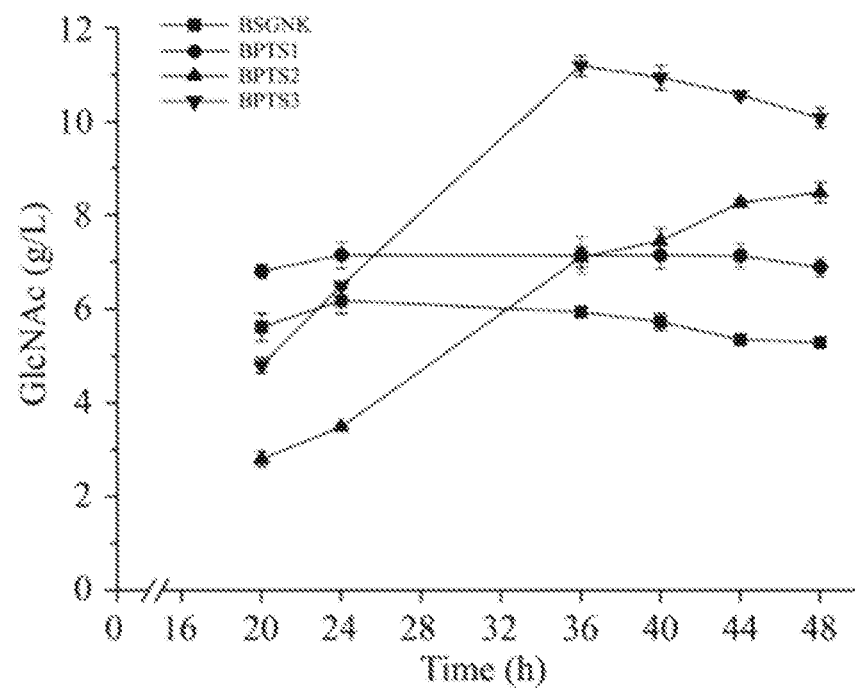
FIG. 2 is a graph showing the comparison of GlcNAc titer of the strains BSGNK, BPTS1, BPTS2 and BPTS3 during fermentation.

It can be seen from FIGS. 1-2 that the strain BPTS1 produced GlcNAc to a higher concentration than BSGNK by 7.14 g/L in the flask cultivation, which was 1.16-fold of that of BSGNK, and deletion of phosphoenolpyruvate carboxykinase encoding gene pckA had little influence on cell growth. The results indicate that deletion of phosphoenolpyruvate carboxykinase encoding gene pckA is benefit for the GlcNAc synthesis.

Embodiment 6

Effects of Deletion of Pyruvate Kinase Encoding Gene pyk on Cell Growth and GlcNAc Production To determine the effects of deletion of pyruvate kinase encoding gene pyk on cell growth and GlcNAc production, the strains BPTS2 and BPTS1 were inoculated with an inoculum size of 5% (v/v) into 500-mL shake flasks each containing 95 mL of fermentation medium. And then, fermentation was carried out at 220 rpm and 37° C. for 48 h on rotary shakers.

Figure 3:
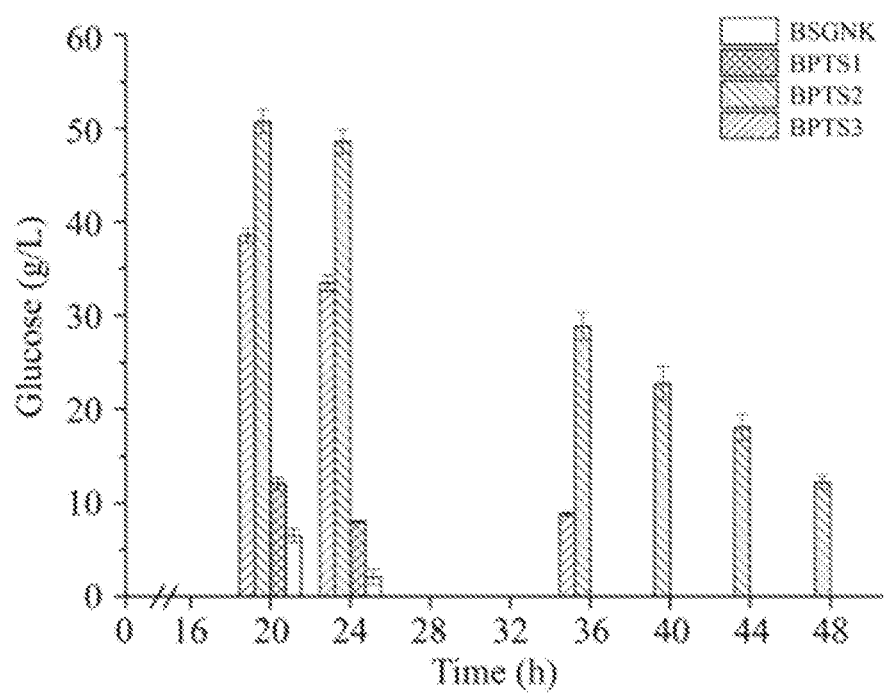
FIG. 3 is a graph showing the comparison of the residual glucose concentration of the strains BSGNK, BPTS1, BPTS2 and BPTS3 during fermentation.

It can be seen from FIG. 2 that the strain BSPT2 produced GlcNAc to a higher concentration than BPTS1 by 8.5 g/L in the flask cultivation, which was 1.18-fold of that of BPTS1. However, deletion of pyruvate kinase encoding gene pyk leaded to the low glucose consumption rate and decreased DCW. FIG. 3 shows the time profile of glucose consumption of BSGNK, BPTS1, BPTS2, BPTS3 in shake flask. The residual glucose concentration of BPTS2 was 12.2 g/L. This was thought to be the non-optimal TCA flux and reduced glycolytic flux.

Embodiment 7

Overexpression of Pyruvate Carboxylase Encoding Gene pycA to Facilitate Cell Growth It is possible that the overexpression of pycA can lead more pyruvate to synthesize OAA and facilitates the glutamine synthesis. Finally, we tested the effects of overexpression of pyruvate carboxylase to cell growth and GlcNAc production. It can be seen from FIGS. 1-2 that the overexpression of pycA can facilitate cell growth, and the glucose consumption rate of BPTS3 was improved than that of BPTS2. Finally, the GlcNAc production of BPTS3 reached 11.3 g/L, which was 32.8% higher than that of BPTS2 and 1.84-fold of that of BSGNK.

FIGS. 1-3 show the effects of deletion of phosphoenolpyruvate carboxykinase encoding gene pckA and pyruvate kinase encoding gene pyk and overexpression of pyruvate carboxylase encoding gene pycA on cell growth, GlcNAc production and glucose consumption.

Table 1 shows the comparison of the maximum GlcNAc titer, the maximum DCW and the GlcNAc productivity of BSGNK, BPTS1, BPTS2, BPTS3 in shake flask fermentation system.

TABLE 1

| Strains | The maximum GlcNAc titer (g/L) | The maximum DCW (g/L) | GlcNAc productivity (g/L/h) |
|---|---|---|---|
| BSGNK | 6.17 | 7.17 | 0.036 |
| BPTS1 | 7.14 | 6.81 | 0.044 |
| BPTS2 | 8.48 | 6.08 | 0.030 |
| BPTS3 | 11.3 | 6.03 | 0.052 |

The above preferred embodiments are described for illustration only, and are not intended to limit the scope of the invention. It should be understood, for a person skilled in the art, that various improvements or variations can be made therein without departing from the spirit and scope of the invention, and these improvements or variations should be covered within the protecting scope of the invention.

What is claimed is:

1. A method for improving GlcNAc production of recombinant *Bacillus Subtilis* comprising deletion of phosphoenolpyruvate carboxykinase encoding gene pckA, deletion of pyruvate kinase encoding gene pyk, as well as overexpression of pyruvate carboxylase encoding gene pycA in the recombinant *Bacillus Subtilis*.

2. The method as claimed in claim 1, wherein the recombinant *Bacillus Subtilis* is BSGNK which is obtained by overexpressing a glucosamine-6-phosphate synthase glms under the control of an inducible promoter PxylA and GlcN-6-phosphate N-acetyltransferase GNA1 under the control of a constitutive promoter P43 in the basis of deleting nagP, gamP, nagA, nagB, gamA and glck of *Bacillus Subtilis* 168.

3. The method as claimed in claim 1, wherein deletion of phosphoenolpyruvate carboxykinase encoding gene pckA comprises step of constructing a pckA disrupt cassette which includes a pckA upstream homology sequence, a zeocin resistant gene expression cassette, and a pckA downstream homology sequence, from *Bacillus Subtilis* 168.

4. The method as claimed in claim 3, wherein the length of the pckA upstream homology sequence is 0.5-1.5 kb, and the length of the pckA downstream homology sequence is 0.5-1.5 kb.

5. The method as claimed in claim 4, wherein the DNA sequence of the pckA disrupt cassette is shown as SEQ ID NO.1.

6. The method as claimed in claim 1, wherein deletion of pyruvate kinase encoding gene pyk comprises step of constructing a pyk disrupt cassette which includes a pyk upstream homology sequence, a zeocin resistant gene expression cassette, and a pyk downstream homology sequence, from *B. subtilis* 168.

7. The method as claimed in claim 6, wherein the length of the pyk upstream homology sequence is 0.5-1.5 kb, and the length of the pyk downstream homology sequence is 0.5-1.5 kb.

8. The method as claimed in claim 7, wherein the DNA sequence of the pyk disrupt cassette is shown as SEQ ID NO.2.

9. The method as claimed in claim 1, wherein the pyruvate carboxylase pycA is overexpressed under the control of a constitutive promoter P43 and replacing a start codon GTG with ATG.

10. The method as claimed in claim 9, wherein overexpression of pyruvate carboxylase encoding gene pycA further comprises step of constructing a pycA overexpressed cassette which includes a pycA upstream homology sequence, a zeocin resistant gene expression cassette, a P43 strong promoter, and a pycA sequence with replacing the start codon GTG with ATG, from *B. subtilis* 168.

11. The method as claimed in claim 10, wherein the length of the pycA upstream homology sequence is 0.5-1.5 kb.

12. The method as claimed in claim 11, wherein the DNA sequence of the pycA overexpressed cassette is shown as SEQ ID NO.3.

* * * * *